United States Patent
Kuo et al.

(10) Patent No.: US 9,670,445 B1
(45) Date of Patent: Jun. 6, 2017

(54) MICROFLUIDICS SENSOR PACKAGE FABRICATION METHOD AND STRUCTURE

(71) Applicant: Amkor Technology, Inc., Chandler, AZ (US)

(72) Inventors: Bob Shih-Wei Kuo, Chandler, AZ (US); Russell Scott Shumway, Mesa, AZ (US)

(73) Assignee: Amkor Technology, Inc., Tempe, AZ (US)

( * ) Notice: Subject to any disclaimer, the term of this patent is extended or adjusted under 35 U.S.C. 154(b) by 933 days.

(21) Appl. No.: 13/793,541

(22) Filed: Mar. 11, 2013

(51) Int. Cl.
    *B01L 3/00* (2006.01)
    *C12M 1/40* (2006.01)
    *H05K 3/10* (2006.01)

(52) U.S. Cl.
    CPC .............. *C12M 21/18* (2013.01); *H05K 3/10* (2013.01)

(58) Field of Classification Search
    CPC ...................................................... C12M 21/18
    See application file for complete search history.

(56) References Cited

U.S. PATENT DOCUMENTS

| | | | |
|---|---|---|---|
| 5,134,340 A * | 7/1992 | Haitz | B41J 2/45 257/88 |
| 6,455,927 B1 | 9/2002 | Glenn et al. | |
| 6,875,619 B2 * | 4/2005 | Blackburn | B01J 19/0093 435/287.1 |
| 2005/0231551 A1 * | 10/2005 | Gibson | B41J 2/14008 347/45 |

OTHER PUBLICATIONS

Kuo et al., "MEMS Package Fabrication Method and Structure," U.S. Appl. No. 13/766,171, filed Feb. 13, 2013.
No author provided, "Polymerase chain reaction," 14 pages, Retrieved on Jan. 8, 2013 from URL: <http://en.wikipedia.org/wiki/Polymerase_chain_reaction>.

* cited by examiner

*Primary Examiner* — Jyoti Nagpaul
(74) *Attorney, Agent, or Firm* — McAndrews, Held & Malloy, Ltd.

(57) ABSTRACT

A microfluidics sensor package includes a microfluidics sensor die having an active surface, bond pads on the active surface, and an active area on the active surface. A standoff pattern is formed on the active surface to extend to a precise height above the active surface. A lid is mounted to the standoff pattern by a lid adhesive. By using the standoff pattern to precisely space the lid above the active surface, a microfluidics cavity between the lid and the active surface is precisely created allowing for precise control of fluid flowing through the microfluidics cavity. By precisely controlling the flow of fluid through the microfluidics cavity, accurate results, e.g., of the laboratory functions performed on the fluid, are provided.

18 Claims, 17 Drawing Sheets

Microfluidics sensor package fabrication method 100

US 9,670,445 B1

MICROFLUIDICS SENSOR PACKAGE FABRICATION METHOD AND STRUCTURE

TECHNICAL FIELD

The present application relates to the field of electronics, and more particularly, to methods of forming electronic component packages and related structures.

BACKGROUND

A microfluidics sensor chip deals with the behavior, precise control, and manipulation of fluids that are geometrically constrained to a small scale. One example of a microfluidics sensor chip is a polymerase chain reaction (PCR) chip, sometimes also known as one type of a Lab-On-a-Chip (LOC).

The polymerase chain reaction (PCR) is a fundamental molecular biology technique that enables the selective amplification of DNA sequences, which is useful for expanded use of rare samples such as stem cells, biopsies, and circulating tumor cells. A PCR chip is a device that integrates one or several laboratory functions, e.g., the PCR, on a single chip. To provide accurate results, the flow of fluid within the PCR chip must be precisely controlled.

BRIEF DESCRIPTION OF THE DRAWINGS

In the following description, the same or similar elements are labeled with the same or similar reference numbers.

DETAILED DESCRIPTION

Figure 7:
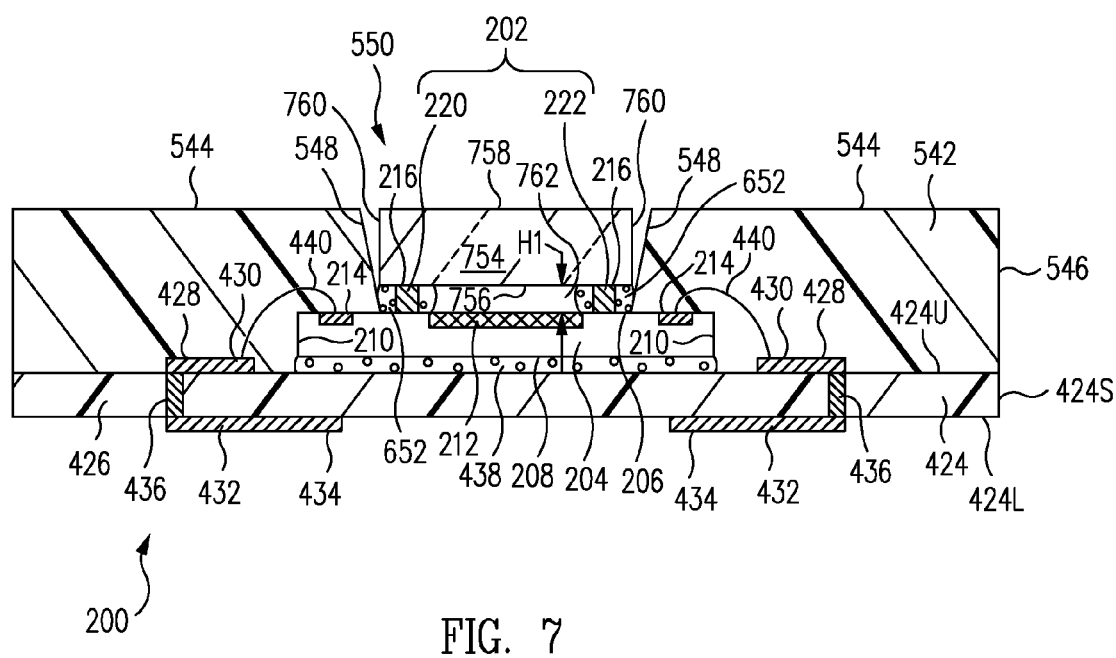

As an overview and in accordance with one embodiment, referring to FIG. 7, a microfluidics sensor package 200 includes a microfluidics sensor die 204 having an active surface 206, bond pads 214 on active surface 206, and an active area 212 on active surface 206. A standoff pattern 202 is formed on active surface 206 to extend to a precise height H1 above active surface 206. A lid 754 is mounted to standoff pattern 202 by a lid adhesive 652.

By using standoff pattern 202 to precisely space lid 754 above active surface 206, a microfluidics cavity 762 between lid 754 and active surface 206 is precisely created allowing for precise control of fluid flowing through microfluidics cavity 762. By precisely controlling the flow of fluid through microfluidics cavity 762, accurate results, e.g., of the laboratory functions performed on the fluid, are provided.

Figure 1:
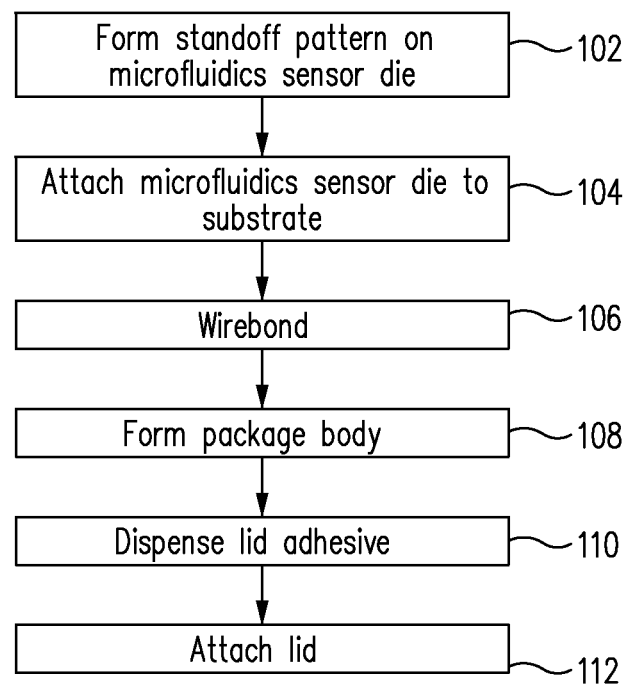
FIG. 1 is a block diagram of a microfluidics sensor package fabrication method in accordance with one embodiment.
Figure 2:
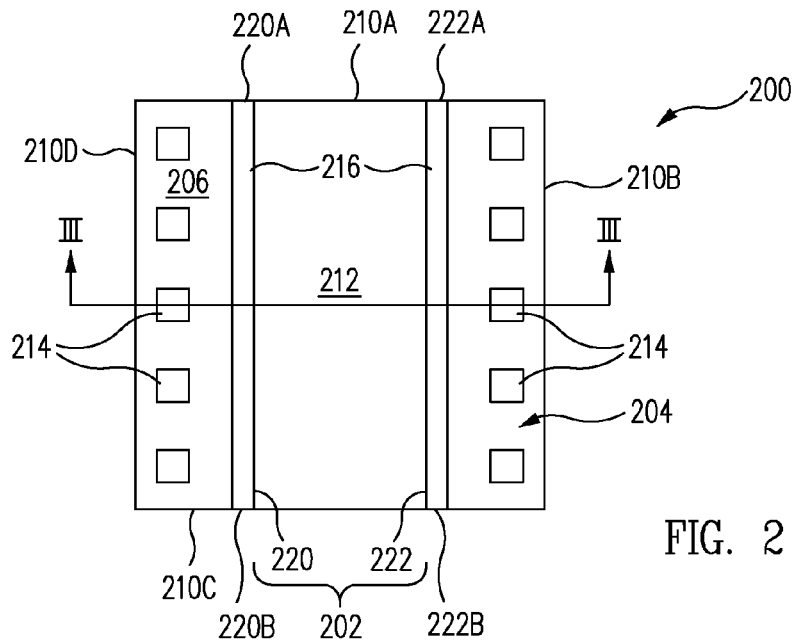
FIG. 2 is a top plan view of a microfluidics sensor package during fabrication in accordance with one embodiment.
Figure 3:
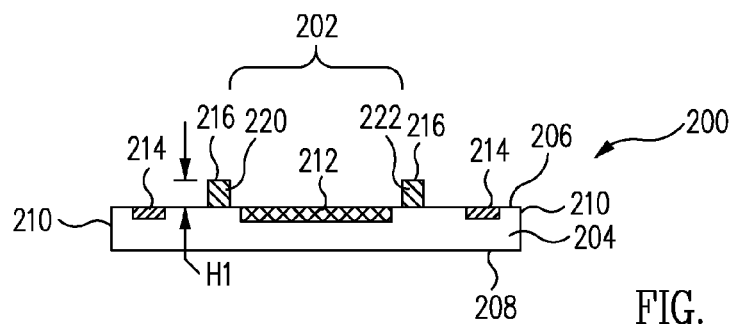
FIG. 3 is a cross-sectional view of the microfluidics sensor package of FIG. 2 along the line III-III in accordance with one embodiment.

Now in more detail, FIG. 1 is a block diagram of a microfluidics sensor package fabrication method 100 in accordance with one embodiment. FIG. 2 is a top plan view of a microfluidics sensor package 200 during fabrication in accordance with one embodiment. FIG. 3 is a cross-sectional view of microfluidics sensor package 200 of FIG. 2 along the line III-III in accordance with one embodiment.

Referring now to FIGS. 1, 2, and 3 together, in a form standoff pattern on microfluidics sensor die operation 102, a standoff pattern 202 is formed on a microfluidics sensor die 204.

More particularly, microfluidics sensor die 204 includes an active surface 206 and an opposite inactive surface 208. Microfluidics sensor die 204 further includes sides 210A, 210B, 210C, 210D, collectively sides 210, extending perpendicularly between active surface 206 and inactive surface 208. Although various features may be described as parallel, perpendicular, or having other relations, in light of this disclosure, those of skill in the art will understand that the features may not be exactly parallel or perpendicular, but only substantially parallel or perpendicular, e.g., to within accepted manufacturing tolerances.

Formed on active surface 206 are an active area 212 and one or more bond pads 214. Active area 212 is a region on active surface 206 to which a precisely controlled flow of fluid is to be provided as described below. For example, active area 212 performs a polymerase chain reaction (PCR) function on the fluid which contacts active area 212. Illustratively, microfluidics sensor die 204 is a polymerase chain reaction (PCR) chip, sometimes also known as one type of a Lab-On-a-Chip (LOC). However, in other embodiments, microfluidics sensor die 204 is another type of die to which a precisely controlled flow of fluid is to be provided. Illustratively, microfluidics sensor die 204 is used in diagnostic, DNA screening, and/or pharmaceutical applications.

Standoff pattern 202 is formed on active surface 206. In one embodiment, standoff pattern 202 is formed outside of active area 212. However, if formation of standoff pattern 202 on active area 212 does not adversely affect operation of microfluidics sensor die 204 and/or is otherwise desirable, standoff pattern 202 is formed partially or entirely on active area 212 in accordance with various embodiments.

Standoff pattern 202 is formed of a non-collapsible and inflexible material, e.g., a material that does not collapse during normal process heating of microfluidics sensor package 200 during fabrication and use. Illustratively, standoff pattern 202 is formed of a metal, e.g., copper. In one embodiment, standoff pattern 202 is formed by plating although can be formed using other techniques in other embodiments.

Standoff pattern 202 extends to a very precise height H1 above active surface 206 of microfluidics sensor die 204. More particularly, standoff pattern 202 includes a lid surface 216 at height H1 above active surface 206 of microfluidics sensor die 204. As discussed below, a lid will be pressed against lid surface 216 to locate the lid precisely at height H1 above active surface 206 of microfluidics sensor die 204.

Sides 210A, 210C are parallel to one another and perpendicular to sides 210B, 210D, which are parallel to one another. Sides 210A, 210C are sometimes called fluid port sides 210A, 210C as fluid generally flows in a direction parallel to sides 210B, 210D and between sides 210A, 210C.

In accordance with this embodiment, bond pads 214 are directly adjacent sides 210B, 210D. Accordingly, sides 210B, 210D are sometimes called bond pad sides 210B, 210D. However, in other embodiments, bond pads 214 are adjacent one or more of any of sides 210.

In accordance with this embodiment, standoff pattern 202 includes a first bar 220 and a second bar 222, sometimes called low profile metallic bars formed with high precision or bump bars. Bars 220, 222 are parallel to sides 210B, 210D and extend between sides 210A, 210C. More particularly, bar 220 includes bar ends 220A, 220B located at sides 210A, 210C, respectively. Similarly, bar 222 includes bar ends 222A, 222B located at sides 210A, 210C, respectively.

Bars 220, 222, and generally standoff pattern 202, define an area of active surface 206, which includes active area 212. In one embodiment, bars 220, 222 surround active area 212 around a perimeter of active area 212 yet do not extend into active area 212. Further, bars 220, 222 do not encompass and leave exposed bond pads 214. Generally, bars 220, 222 are located between active area 212 and bond pads 214. However, if formation of bars 220, 222 on active area 212 does not adversely affect operation of microfluidics sensor die 204 and/or is otherwise desirable, bars 220, 222 are formed partially or entirely on active area 212 in accordance with various embodiments.

In accordance with this embodiment, lid surface 216 is defined by the uppermost surfaces, e.g., two rectangular or curved thin strips, of bars 220, 222 at height H1 above active surface 206 of microfluidics sensor die 204.

Figure 4:
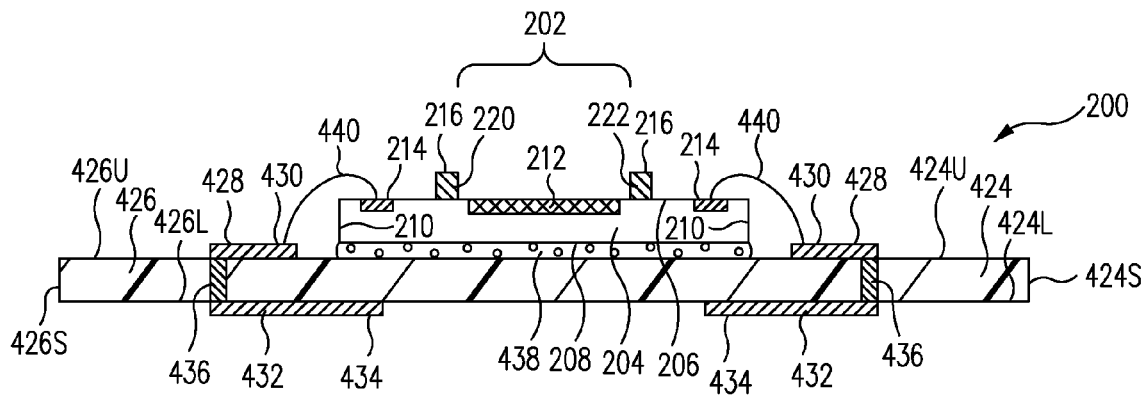
FIGS. 4, 5, 6, 7 are cross-sectional views of the microfluidics sensor package of FIG. 3 at further stages during fabrication in accordance with various embodiments.

FIG. 4 is a cross-sectional view of microfluidics sensor package 200 of FIG. 3 at a further stage during fabrication in accordance with one embodiment. Referring now to FIGS. 1 and 4 together, from form standoff pattern on microfluidics sensor die operation 102, flow moves to an attach microfluidics sensor die to substrate operation 104. In attach microfluidics sensor die to substrate operation 104, microfluidics sensor die 204 is attached to a substrate 424.

Substrate 424 includes a substrate core 426 including an upper, e.g., first, surface 426U and an opposite lower, e.g., second, surface 426L. Substrate core 426 further includes sides 426S extending perpendicularly between upper surface 426U and lower surface 426L. Substrate core 426 is a dielectric material such as laminate, ceramic, printed circuit board material, or other dielectric material.

Formed on upper surface 426U of substrate core 426 are electrically conductive upper, e.g., first, traces 428, e.g., formed of copper. Upper traces 428 include terminals 430, sometimes called bond fingers.

Formed on lower surface 426L of substrate core 426 are lower, e.g., second, traces 432. Lower traces 432 including electrically conductive lands 434.

Lower traces 432 are electrically connected to upper traces 428 by electrically conductive vias 436 extending through substrate core 426 between upper surface 426U and lower surface 426L.

Although upper traces 428 are illustrated as being on upper surface 426U of substrate core 426, in other embodiments, upper traces 428 are partially or totally embedded into substrate core 426 at upper surface 426U. Similarly, although lower traces 432 are illustrated as being on lower surface 426L of substrate core 426, in other embodiments, lower traces 432 are partially or totally embedded into substrate core 426 at lower surface 426L.

Although not illustrated, substrate 424 can include dielectric solder masks on upper surface 426U and lower surface 426L. For example, the upper solder mask protects, i.e., covers, first portions of upper traces 428 while exposing second portions, e.g., terminals 430, of upper traces 428. The lower solder mask protects, i.e., covers, first portions of lower traces 432 while exposing second portions, e.g., lands 434, of lower traces 432. The upper and lower solder masks are optional, and in one embodiment, are not formed.

Generally, substrate 424 includes an upper, e.g., first, surface 424U and an opposite lower, e.g., second, surface 424L. Upper surface 424U is defined by the upper solder mask, by upper surface 426U of substrate core 426, and/or by any other structure which forms upper surface 424U of substrate 424. Similarly, lower surface 424L is defined by the lower solder mask, by lower surface 426L of substrate core 426, and/or by any other structure which forms lower surface 424L of substrate 424.

Substrate 424 further includes sides 424S extending perpendicularly between upper surface 424U and lower surface 424L.

Although a particular electrically conductive pathway between upper traces 428 and lower traces 432 is described above, other electrically conductive pathways can be formed. For example, contact metallizations can be formed between the various electrical conductors.

Further, instead of straight though vias 436, in one embodiment, a multilayer substrate includes a plurality of vias and/or internal traces that form the electrical interconnection between upper traces 428 and lower traces 432.

In one embodiment, interconnection balls, e.g., lead free solder balls, are formed on lands 434 to provide a Ball Grid Array (BGA). In one embodiment, the interconnection balls are not formed and lands 434 are distributed in an array thus forming a Land Grid Array (LGA). However, in other embodiments, other package configurations other than a LGA and a BGA are used. For example, a lead frame configuration is used as discussed further below.

In accordance with this embodiment, in attach microfluidics sensor die to substrate operation 104, inactive surface 208 of microfluidics sensor die 204 is attached to upper surface 424U of substrate 424 by an adhesive 438.

From attach microfluidics sensor die to substrate operation 104, flow moves to a wirebond operation 106. In wirebond operation 106, bond pads 214 are electrically connected to terminals 430 of upper traces 428 of substrate 424 by bond wires 440.

Figure 5:
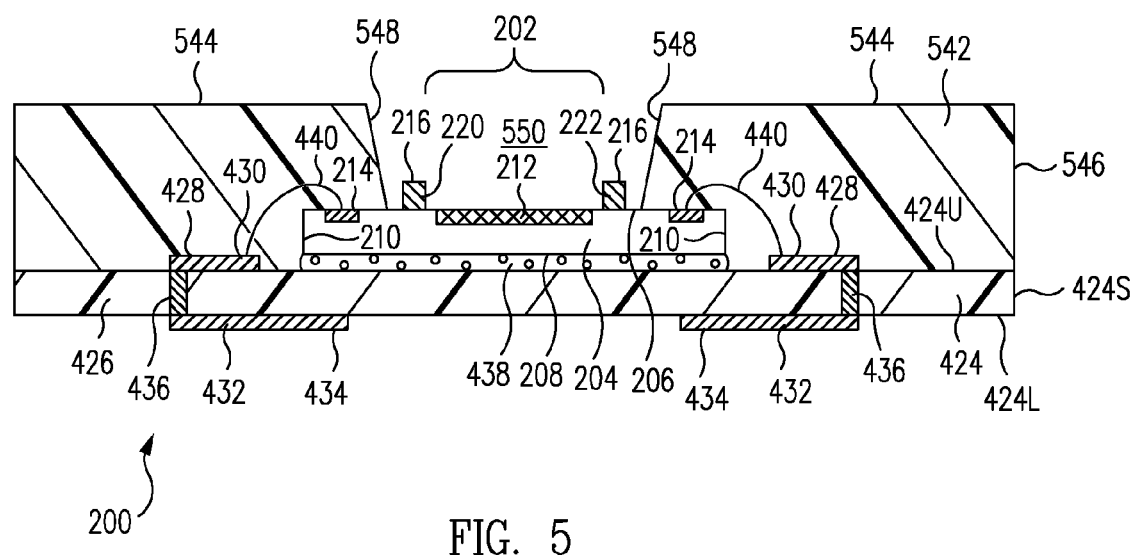

FIG. 5 is a cross-sectional view of microfluidics sensor package 200 of FIG. 4 at a further stage during fabrication in accordance with one embodiment. Referring now to FIGS. 1 and 5 together, from wirebond operation 106, flow moves to a form package body operation 108. In form package body operation 108, a package body 542 is formed, e.g., by film assist molding.

Package body 542 is a dielectric material, e.g., electronic molding compound (EMC), encapsulant, or other dielectric material. Package body 542 encloses and protects bond pads 214, bond wires 440, and upper surface 424U of substrate 424. By enclosing bond pads 214 and bond wires 440, package body 542 insures segregation of bond pads 214 and bond wires 440 from fluid as discussed below. Package body 542 is sometimes said to be formed by over molding the assembly.

Package body 542 includes a principal surface 544, sides 546, and lid cavity sidewalls 548. Principal surface 544 is the uppermost surface of package body 542 and is parallel to upper surface 424U of substrate 424. Sides 546 extend between upper surface 424U of substrate 424 and principal surface 544. In this embodiment, sides 546 are perpendicular to principal surface 544 and coplanar to sides 424S of substrate 424. However, in another embodiment, sides 546 are located inward of sides 424S of substrate 424, e.g., an outer peripheral portion of upper surface 424U of substrate 424 is exposed from package body 542. Further, instead of being perpendicular to upper surface 424U of substrate 424, in one embodiment, sides 546 are slanted, e.g., inward.

Lid cavity sidewalls 548 of package body 542 and active surface 206 of microfluidics sensor die 204 define a lid cavity 550. Bars 220, 222 and active area 212 are exposed to the exterior, i.e., the ambient environment, through lid cavity 550.

More particularly, lid cavity sidewalls 548 extend from active surface 206 of microfluidics sensor die 204 to principal surface 544 of package body 542. In accordance with this embodiment, lid cavity sidewalls 548 extend from a region of active surface 206 located between bond pads 214 and bars 220, 222. Accordingly, package body encloses bond pads 214 yet exposes bars 220, 222, at least partially.

Figure 6:
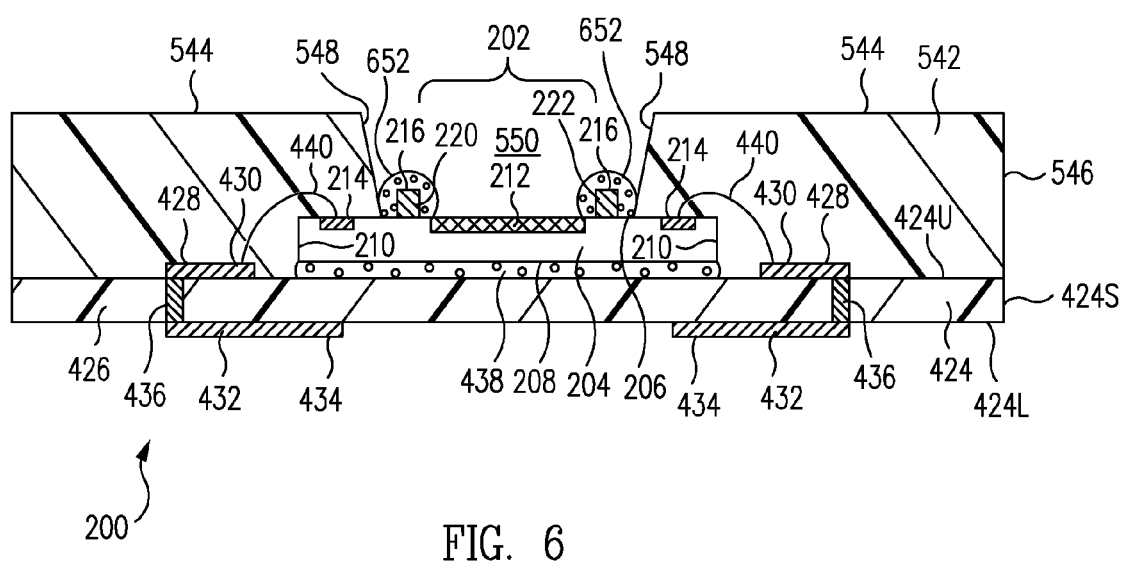

FIG. 6 is a cross-sectional view of microfluidics sensor package 200 of FIG. 5 at a further stage during fabrication in accordance with one embodiment. Referring now to FIGS. 1 and 6 together, from form package body operation 108, flow moves to a dispense lid adhesive operation 110. In dispense lid adhesive operation 110, a lid adhesive 652 is dispensed within lid cavity 550. More particularly, lid adhesive 652 is dispensed on bars 220, 222, and generally on standoff pattern 202.

FIG. 7 is a cross-sectional view of microfluidics sensor package 200 of FIG. 6 at a further stage during fabrication in accordance with one embodiment. Referring now to FIGS. 1 and 7 together, from dispense lid adhesive operation 110, flow moves to an attach lid operation 112. In attach lid operation 112, a lid 754 is attached to bars 220, 222, and generally to standoff pattern 202.

Lid 754 includes a planar inner, e.g., first, surface 756, an opposite outer, e.g., second, surface 758, and sides 760 extending perpendicularly between inner surface 756 and outer surface 758. Inner surface 756 is pressed into lid adhesive 652 and into contact with lid surface 216 of standoff pattern 202. Accordingly, inner surface 756 is coplanar with lid surface 216 and thus precisely located at height H1 above active surface 206. Lid adhesive 652 is then cured if necessary thus bonding lid 754 to standoff pattern 202 at precise height H1 above active surface 206.

Lid 754 is mounted above and spaced apart from active area 212. More particularly, inner surface 756 of lid 754, lid adhesive 652, and active surface 206 define a microfluidics cavity 762, sometimes called a cavity 762. As discussed further below, fluid is introduced into cavity 762 to contact active area 212 for analysis, e.g., a PCR analysis.

In one embodiment, lid 754 is glass, e.g., borosilicate glass. In accordance with this embodiment, lid 754 is transparent allowing ready visualization of fluid flowing through microfluidics cavity 762. In this manner, undesirable bubble entrapment within microfluidics cavity 762 is readily detected. However, in other embodiments, lid 754 is opaque.

Generally, lid 754 is made of a material having sufficient integrity, e.g., rigid and nonflexible, to provide a desired flatness of inner surface 756. Examples of materials of lid 754 include glass, ceramic, metal, and plastic.

In FIG. 7, outer surface 758 of lid 754 is coplanar with principal surface 544 of package body 542. However, in other embodiments, outer surface 758 of lid 754 is above or below principal surface 544 of package body 542 depending upon the thickness of package body 542, standoff pattern 202, and lid 754.

Figure 8:
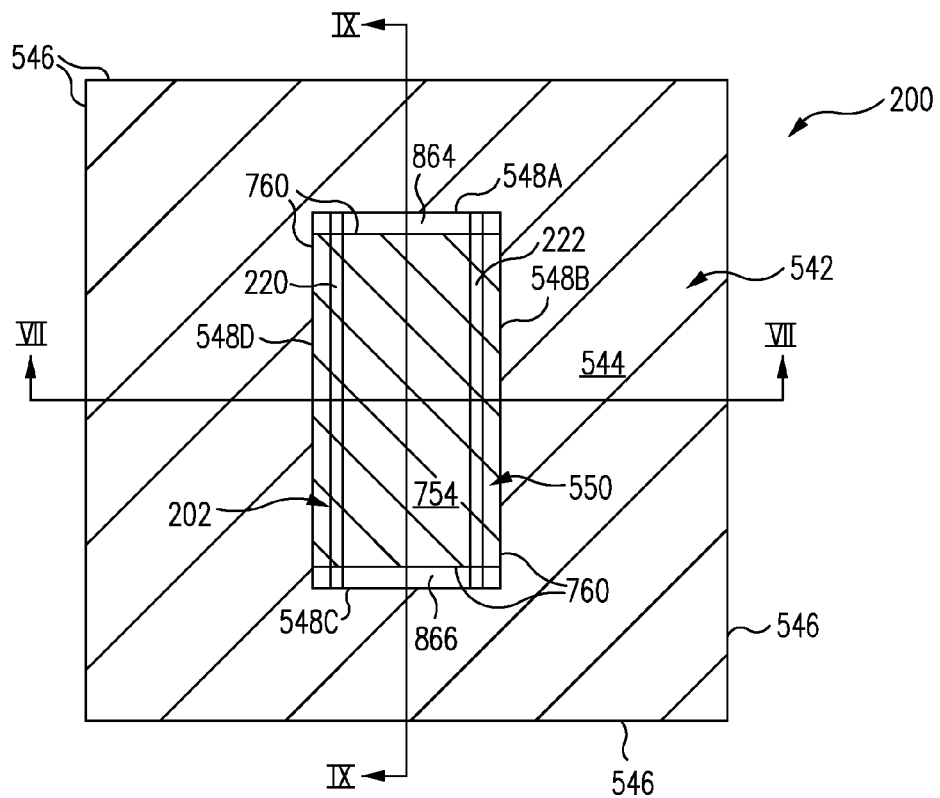
FIG. 8 is a top plan view of the microfluidics sensor package of FIG. 7 in accordance with one embodiment.
Figure 9:
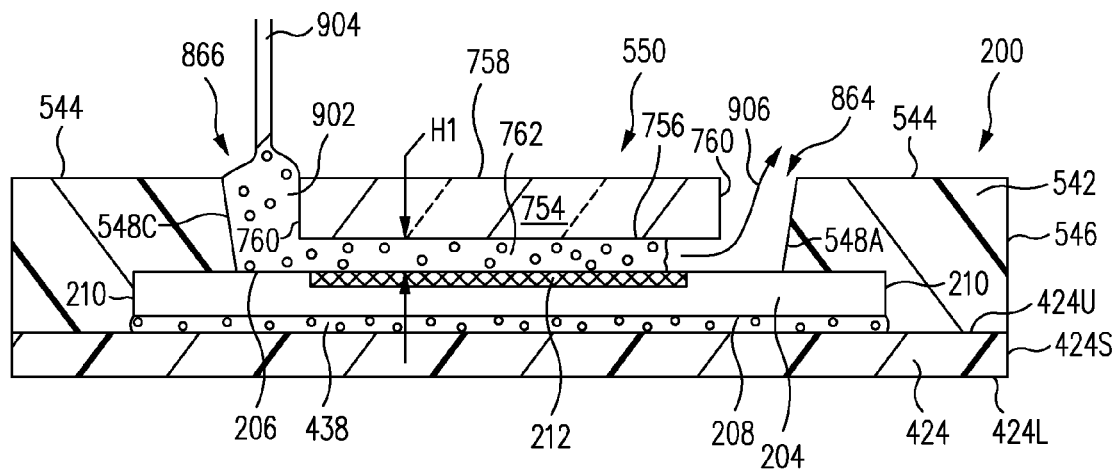
FIG. 9 is a cross-sectional view of the microfluidics sensor package of FIG. 8 along the line IX-IX during use in accordance with one embodiment.

FIG. 8 is a top plan view of microfluidics sensor package 200 of FIG. 7 in accordance with one embodiment. Note the view of FIG. 7 corresponds to a cross-section view of FIG. 8 along the line VII-VII in accordance with one embodiment. FIG. 9 is a cross-sectional view of microfluidics sensor package 200 of FIG. 8 along the line IX-IX during use in accordance with one embodiment.

Referring to FIGS. 7, 8, and 9 together, lid cavity sidewalls 548 include lid cavity sidewalls 548A, 548B, 548C, 548D. Lid cavity sidewalls 548A, 548B, 548C, 548D are collectively referred to as lid cavity sidewalls 548. Lid cavity sidewalls 548A, 548C are parallel to one another and perpendicular to lid cavity sidewalls 548B, 548D, which are parallel to one another. Lid cavity sidewalls 548A, 548C are sometimes called fluid port lid cavity sidewalls 548A, 548C as fluid generally flows in a direction parallel to lid cavity sidewalls 548B, 548D and between lid cavity sidewalls 548A, 548C.

In accordance with this embodiment, bond pads 214 are directly adjacent lid cavity sidewalls 548B, 548D. Accordingly, lid cavity sidewalls 548B, 548D are sometimes called bond pad lid cavity sidewalls 548B, 548D. As illustrated, in accordance with this embodiment, bond pads 214 are directly adjacent lid cavity sidewalls 548B, 548D. However, in other embodiments, bond pads 214 are adjacent one or more of any of lid cavity sidewalls 548.

Paying particular attention now to FIGS. 8 and 9 together, fluid port lid cavity sidewalls 548A, 548C of package body 542 and respective sides 760 of lid 754 define fluid ports 864, 866. More particularly, fluid ports 864, 866 are spaces, sometimes called channels, between fluid port lid cavity sidewalls 548A, 548C and respective sides 760, respectively. Fluid ports 864, 866 extend between the ambient environment and microfluidics cavity 762 and are generally defined between lid 754 and package body 542. Fluid ports 864, 866 are sometimes called entrance and exit ports.

Referring now to FIG. 9, during use of microfluidics sensor package 200, fluid 902 is introduced, e.g., using a dispenser 904, into microfluidics cavity 762 through fluid port 866 (or 864). Fluid 902 entering fluid port 866 (or 864) flows through microfluidics cavity 762, e.g., due to capillary action. Gas 906, e.g., air, within microfluidics cavity 762 is vented through fluid port 864 (or 866) allowing fluid 902 to freely flow through microfluidics cavity 762. Fluid 902 contacts active area 212, which performs one or more functions, e.g., PCR, on fluid 902 as those of skill in the art will understand in light of this disclosure.

By using standoff pattern 202 to precisely space lid 754 above active surface 206, the resultant microfluidics cavity 762 between lid 754 and active surface 206 is precisely created allowing for precise control of fluid 902 flowing through microfluidics cavity 762. By precisely controlling the flow of fluid 902 through microfluidics cavity 762, accurate results, e.g., of the laboratory functions performed on fluid 902, are provided. More particularly, microfluidics cavity 762, sometimes called a gap between lid 754 and active surface 206, has a gap height H1 defined by standoff pattern 202.

Further, by enclosing bond pads 214 and bond wires 440 within package body 542, segregation of bond pads 214 and bond wires 440 from fluid 902 is insured.

Figure 10:
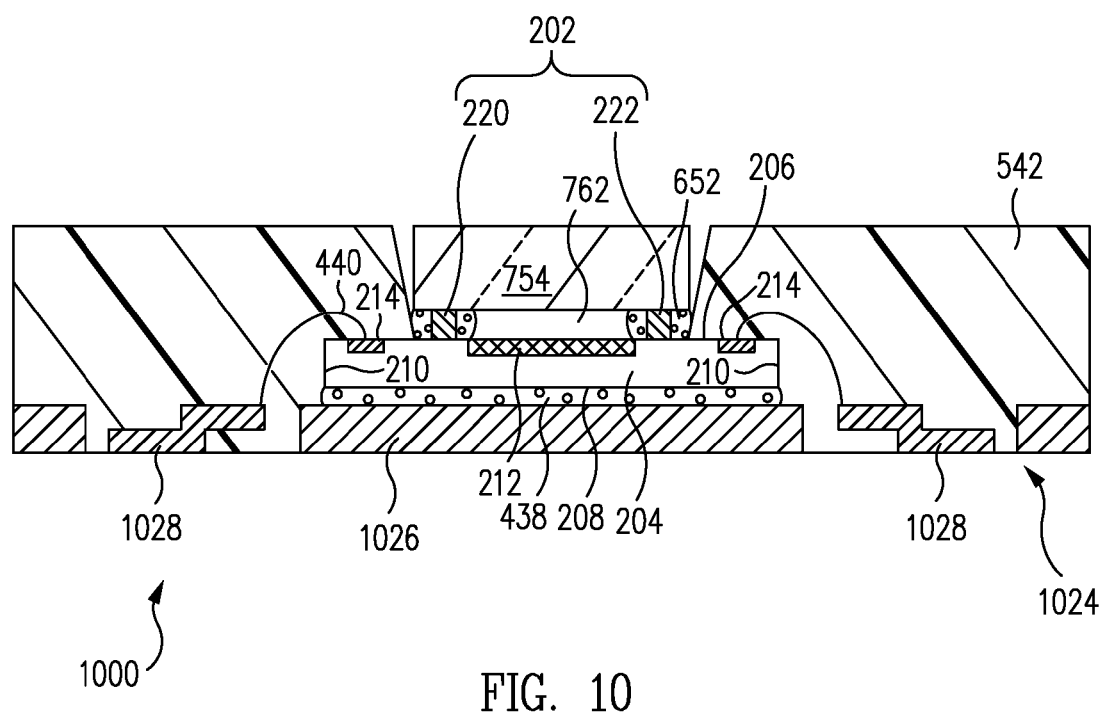
FIG. 10 is a cross-sectional view of a microfluidics sensor package in accordance with another embodiment.

FIG. 10 is a cross-sectional view of a microfluidics sensor package 1000 in accordance with another embodiment. Microfluidics sensor package 1000 of FIG. 10 is similar to microfluidics sensor package 200 of FIG. 7, and only the significant differences shall be discussed below.

In accordance with this embodiment, microfluidics sensor package 1000 includes a lead frame substrate 1024, e.g., a routable lead frame. Inactive surface 208 of microfluidics sensor die 204 is mounted to a die pad 1026 of lead frame substrate 1024 by adhesive 438. Bond pads 214 are electrically connected to leads 1028 of lead frame substrate 1024 by bond wires 440.

Figure 11:
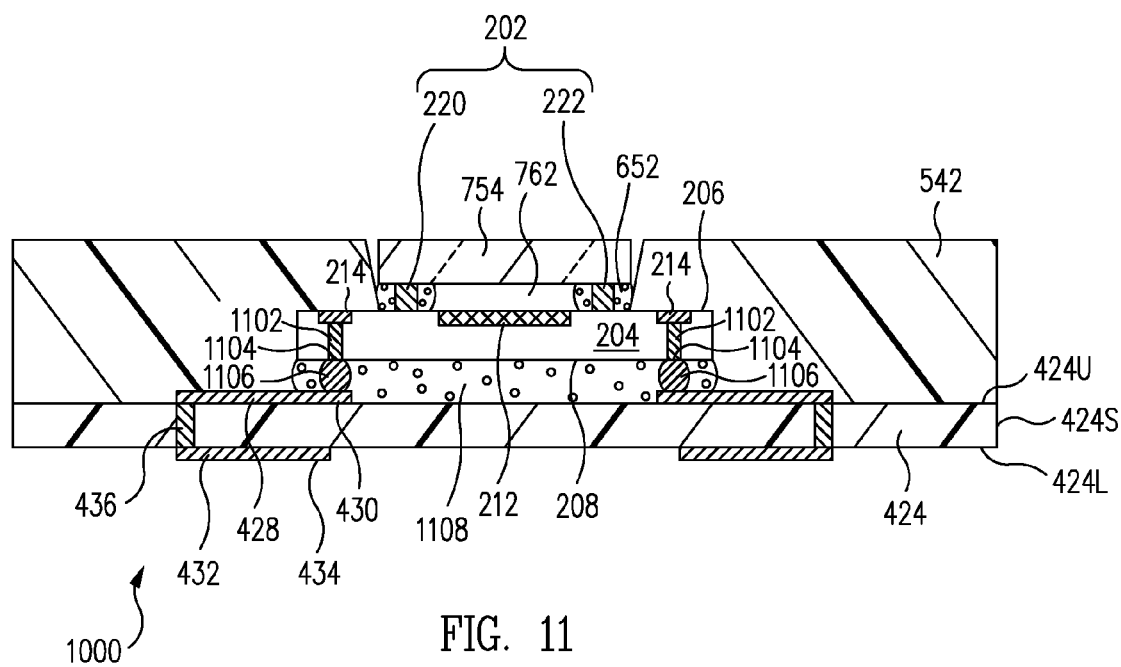
FIG. 11 is a cross-sectional view of a microfluidics sensor package in accordance with yet another embodiment.

FIG. 11 is a cross-sectional view of a microfluidics sensor package 1100 in accordance with yet another embodiment. Microfluidics sensor package 1100 of FIG. 11 is similar to microfluidics sensor package 200 of FIG. 7, and only the significant differences shall be discussed below.

In accordance with this embodiment, through vias 1102, sometimes called through silicon vias (TSVs), are formed within microfluidics sensor die 204. Through vias 1102 extend between active surface 206 and inactive surface 208. Through vias 1102 are formed of an electrically conductive material and are electrically connected to bond pads 214. The ends of through vias 1102 at inactive surface 208 form inactive surface terminals 1104 of microfluidics sensor die 204.

Inactive surface terminals 1104 are physically and electrically connected to terminals 430 of upper traces 428 by flip chip bumps 1106. Optionally, an underfill 1108 is applied between inactive surface 208 of microfluidics sensor die 204 and upper surface 424U of substrate 424 to enclose and protect flip chip bumps 1106.

Figure 12:
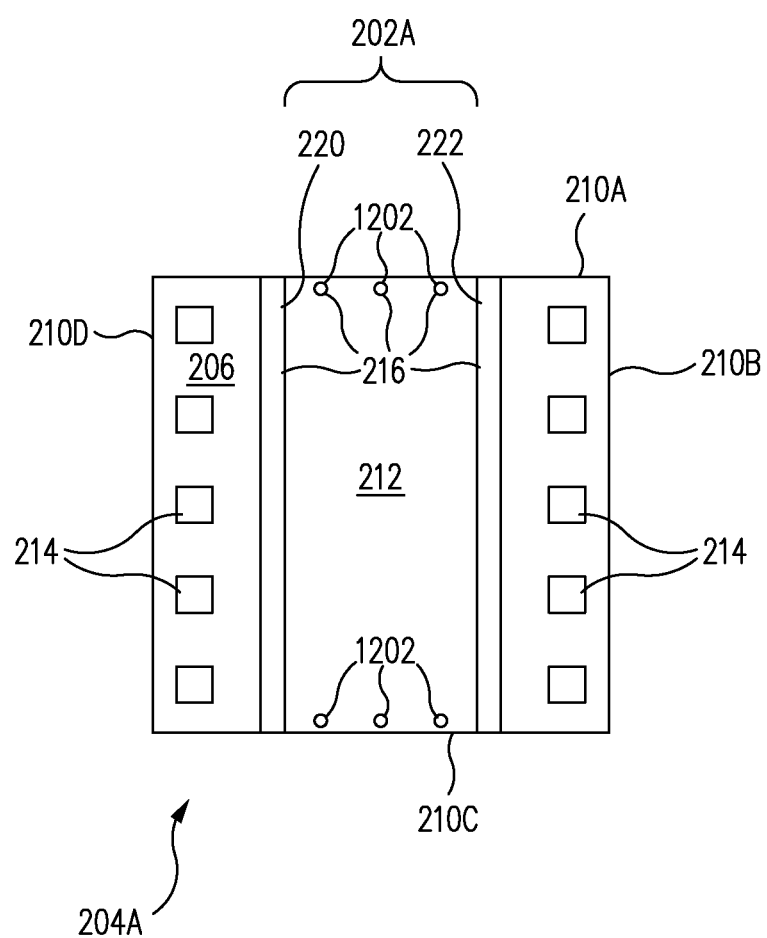
FIG. 12 is a top plan view of a microfluidics sensor die for use in a microfluidics sensor package in accordance with one embodiment.

FIG. 12 is a top plan view of a microfluidics sensor die 204A for use in a microfluidics sensor package in accordance with one embodiment. Microfluidics sensor die 204A of FIG. 12 is substantially similar to microfluidics sensor die 204 of FIG. 2 and only the significant differences are discussed below.

More particularly, referring now to FIG. 12, a standoff pattern 202A further includes one or more dummy bumps 1202. In accordance with this particular embodiment, dummy bumps 1202 are formed directly adjacent sides 210A, 210C and in between bars 220, 222. Dummy bumps 1202 extend to precise height H1 of bars 220, 222, e.g., see height H1 of FIG. 7 for example. Dummy bumps 1202 provide additional support and thus maintain planarity of a lid, e.g., see lid 754 of FIG. 7, mounted to standoff pattern 202A including bars 220, 222 and dummy bumps 1202.

Figure 13:
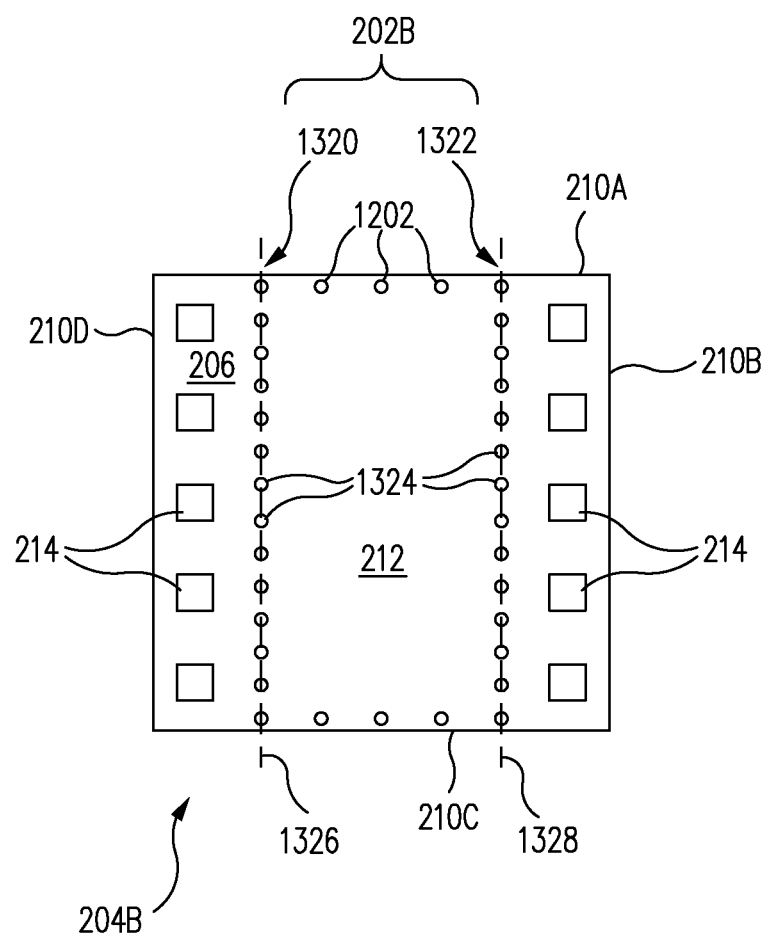
FIG. 13 is a top plan view of a microfluidics sensor die for use in a microfluidics sensor package in accordance with one embodiment.

FIG. 13 is a top plan view of a microfluidics sensor die 204B for use in a microfluidics sensor package in accordance with one embodiment. Microfluidics sensor die 204B of FIG. 13 is substantially similar to microfluidics sensor die 204A of FIG. 12 and only the significant differences are discussed below.

More particularly, referring now to FIGS. 12 and 13 together, a standoff pattern 202B includes first and second bar bump columns 1320, 1322 (see FIG. 13) in place of bars 220, 222 (see FIG. 12). More particularly, instead of continuous bars 220, 222, bar bump columns 1320, 1322 are formed of a plurality of bar bumps 1324, e.g., low profile metallic dots formed with high precision. Accordingly, the location, height, materials, and other features of bars 220, 222 as discussed above is equally applicable to bar bump columns 1320, 1322.

Bar bump column 1320 is formed of a plurality of bar bumps 1324 lying upon a first imaginary line 1326. Bar bump column 1322 is formed of a plurality of bar bumps 1324 lying upon a second imaginary line 1328. Note that the lid adhesive (see lid adhesive 652 of FIG. 7 for example) seals the space between bar bumps 1324.

Figure 14:
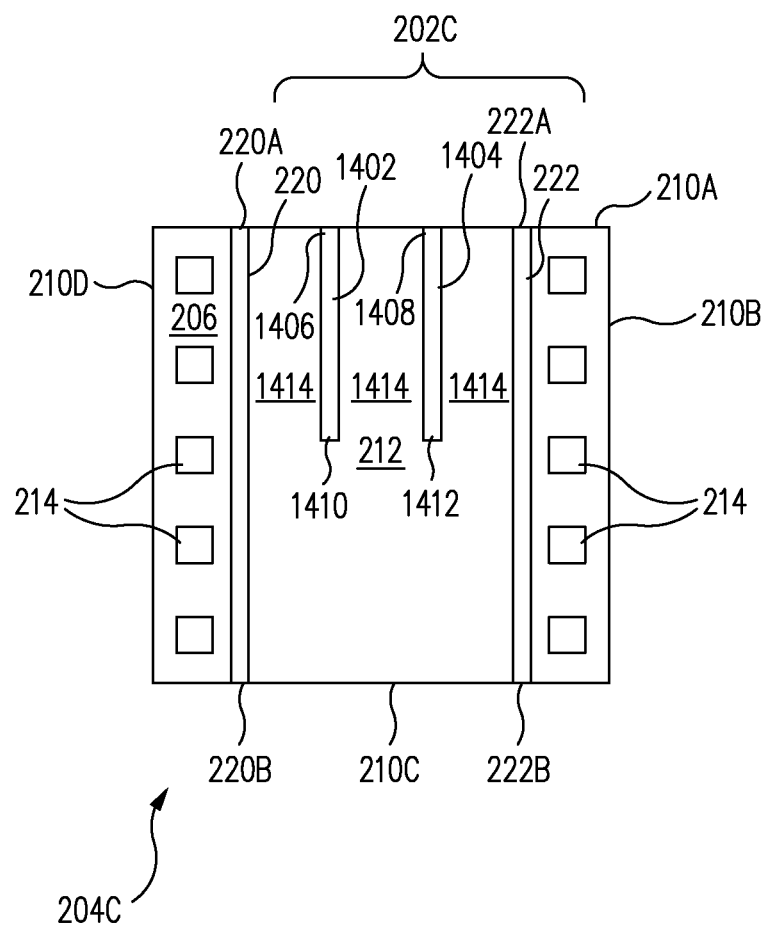
FIG. 14 is a top plan view of a microfluidics sensor die for use in a microfluidics sensor package in accordance with another embodiment.

FIG. 14 is a top plan view of a microfluidics sensor die 204C for use in a microfluidics sensor package in accordance with one embodiment. Microfluidics sensor die 204C of FIG. 14 is substantially similar to microfluidics sensor die 204 of FIG. 2 and only the significant differences are discussed below.

More particularly, referring now to FIG. 14, a standoff pattern 202C further includes one or more sub-channel bars, i.e., two sub-channel bars 1402, 1404 in accordance with this embodiment. Sub-channel bars 1402, 1404 are parallel to sides 210B, 210D, bars 220, 222, and extend towards side 210C from side 210A.

Sub-channel bars 1402, 1404 include port ends 1406, 1408 located at side 210A. Sub-channel bars 1402, 1404 further include leading ends 1410, 1412 located between sides 210A, 210C.

Although sub-channel bars 1402, 1404 extend only partially across the length of microfluidics sensor die 204C and not all the way to side 210C, in another embodiment, sub-channel bars 1402, 1404 extend across the entire length of microfluidics sensor die 204C and all the way to side 210C, i.e., extend between sides 210A, 210C. Stated another way, in another embodiment, leading ends 1410, 1412 of sub-channel bars 1402, 1404 are located at side 210C.

Sub-channel bars 1402, 1404 are formed between bars 220, 222 to subdivide microfluidics cavity 762 into two or more microfluidics sub-cavities 1414. For example, the fluid is subdivided into microfluidics sub-cavities 1414 to contact different regions of active area 212, or for other reasons In one embodiment, sub-channel bars 1402, 1404 extend to precise height H1 of bars 220, 222 (see height H1 of FIG. 7 for example). Sub-channel bars 1402, 1404 provide additional support and thus maintain planarity of a lid, e.g., see lid 754 of FIG. 7, mounted to standoff pattern 202C including bars 220, 222 and sub-channel bars 1402, 1404.

Figure 15:
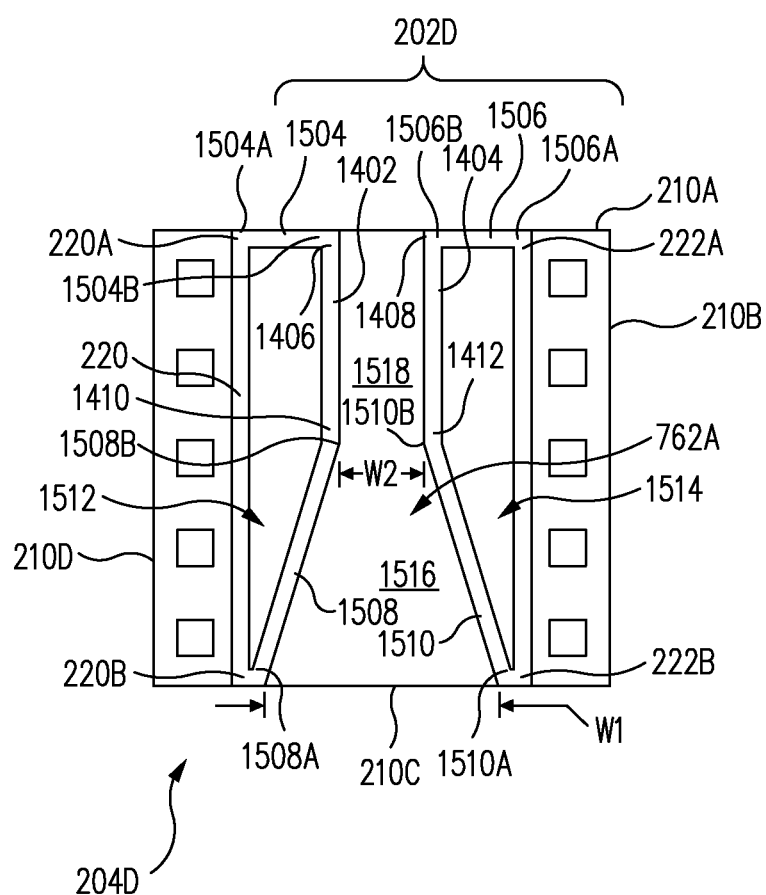
FIG. 15 is a top plan view of a microfluidics sensor die for use in a microfluidics sensor package in accordance with yet another embodiment.

FIG. 15 is a top plan view of a microfluidics sensor die 204D for use in a microfluidics sensor package in accordance with one embodiment. Microfluidics sensor die 204D of FIG. 15 is substantially similar to microfluidics sensor die 204C of FIG. 14 and only the significant differences are discussed below.

More particularly, referring now to FIG. 15, a standoff pattern 202D further includes two end bars 1504, 1506, and two diverter bars 1508, 1510. Standoff pattern 202D provides flow speed control of a fluid flowing through a variable size microfluidics cavity 762A.

End bar 1504 extends parallel to side 210A and between bar end 220A of bar 220 and port end 1406 of sub-channel bar 1402. More particularly, end bar 1504 includes ends 1504A, 1504B. End 1504A is located at bar end 220A of bar 220. End 1504B is located at port end 1406 of sub-channel bar 1402.

Diverter bar 1508 extends between bar end 220B of bar 220 and leading end 1410 of sub-channel bar 1402. More particularly, diverter bar 1508 includes ends 1508A, 1508B. End 1508A is located at bar end 220B of bar 220. End 1508B is located at leading end 1410 of sub-channel bar 1402. Diverter bar 1508 is non-perpendicularly angled relative to side 210C and generally extends inwards and away from side 210D between end 1508A and end 1508B.

Bar 220, end bar 1504, sub-channel bar 1402, and diverter bar 1508 define a first sealed cavity 1512. During use, sealed cavity 1512 is sealed thus avoiding entrance of fluid therein.

End bar 1506 extends parallel to side 210A and between bar end 222A of bar 222 and port end 1408 of sub-channel bar 1404. More particularly, end bar 1506 includes ends 1506A, 1506B. End 1506A is located at bar end 222A of bar 222. End 1506B is located at port end 1408 of sub-channel bar 1404.

Diverter bar 1510 extends between bar end 222B of bar 222 and leading end 1412 of sub-channel bar 1404. More particularly, diverter bar 1510 includes ends 1510A, 1510B. End 1510A is located at bar end 222B of bar 222. End 1510B is located at leading end 1412 of sub-channel bar 1404. Diverter bar 1510 is non-perpendicularly angled relative to side 210C and generally extends inwards and away from side 210B between end 1510A and end 1510B.

Bar 222, end bar 1506, sub-channel bar 1404, and diverter bar 1510 define a second sealed cavity 1514. During use, sealed cavity 1514 is sealed thus avoiding entrance of fluid therein.

Variable size microfluidics cavity 762A includes a variable cavity 1516 and a fixed cavity 1518 in fluid communication with one another. Variable cavity 1516 is defined by diverter bars 1508, 1510 whereas fixed cavity 1518 is defined by sub-channel bars 1402, 1404. Variable cavity 1516 has a width W1 at side 210C and decreases to a second width W2 at fixed cavity 1518 including leading ends 1410, 1412 of sub-channel bars 1402, 1404, respectively. Fixed cavity 1518 has uniform width W2 between variable cavity 1516 including leading ends 1410, 1412 and side 210A.

During use, fluid is introduced near side 210C and flow through variable cavity 1516 to fixed cavity 1518. As the fluid flows through the narrowing variable cavity 1516, i.e., upward in the view of FIG. 15, the fluid flow speed increases.

Conversely, and in accordance with another embodiment, fluid is introduced near side 210A and flows through fixed cavity 1518 to variable cavity 1516. As the fluid flows through the widening variable cavity 1516, i.e., downward in the view of FIG. 15, the fluid flow speed decreases.

In one embodiment, sub-channel bars 1402, 1404, end bars 1504, 1506, and diverter bars 1508, 1510 extend to precise height H1 of bars 220, 222, e.g., see height H1 of FIG. 7 for example. Sub-channel bars 1402, 1404, end bars 1504, 1506, and diverter bars 1508, 1510 provide additional support and thus maintain planarity of a lid, e.g., see lid 754 of FIG. 7, mounted to standoff pattern 202D including bars 220, 222, sub-channel bars 1402, 1404, end bars 1504, 1506, and diverter bars 1508, 1510. At the same time, standoff pattern 202D provides flow speed control of fluid flowing through variable size microfluidics cavity 762A as discussed above.

Although fabrication of a single microfluidics sensor package is described above, in other embodiments, microfluidics sensor packages are simultaneously formed, e.g., in an array, and then singulated into individual microfluidics sensor packages. In one embodiment, form standoff pattern on microfluidics sensor die operation 102 (FIG. 1) is performed on the microfluidics sensor die while still in wafer form.

Figure 16:
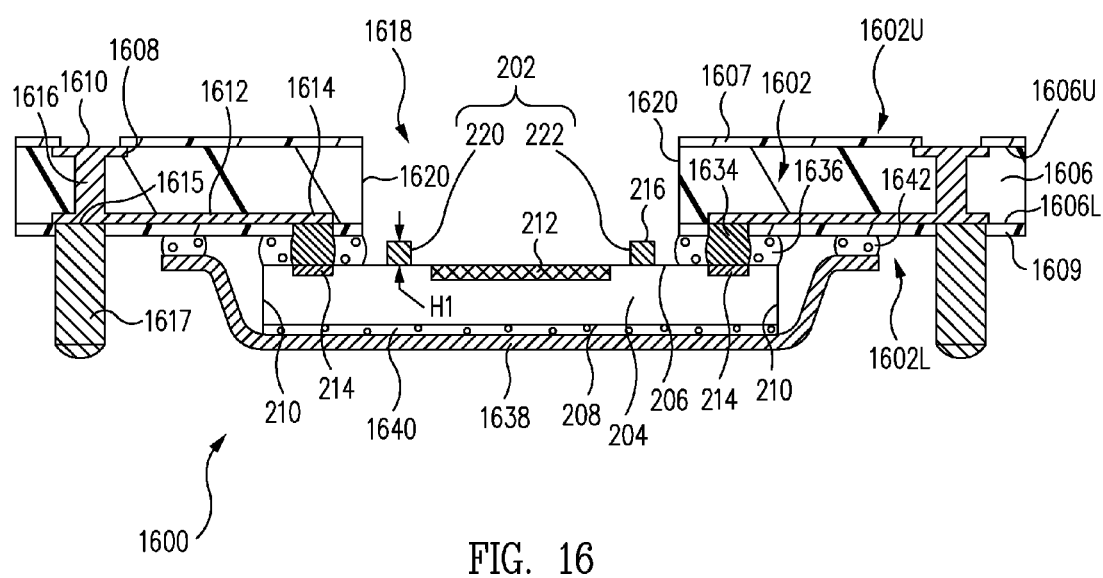
FIG. 16 is a cross-sectional view of a microfluidics sensor package in accordance with another embodiment.

FIG. 16 is a cross-sectional view of a microfluidics sensor package 1600 in accordance with another embodiment. Microfluidics sensor package 1600 includes a substrate 1602. Substrate 1602 includes a substrate core 1606 including an upper, e.g., first, surface 1606U and an opposite lower, e.g., second, surface 1606L. Substrate core 1606 is a dielectric material such as laminate, ceramic, printed circuit board material, or other dielectric material.

Embedded within upper surface 1606U of substrate core 1606 are electrically conductive upper, e.g., first, traces 1608, e.g., formed of copper. Upper traces 1608 include lands 1610.

Embedded within lower surface 1606L of substrate core 1606 are lower, e.g., second, traces 1612. Lower traces 1612 including electrically conductive terminals 1614 and lands 1615.

Lower traces 1612 are electrically connected to upper traces 1608 by electrically conductive vias 1616 extending through substrate core 1606 between upper surface 1606U and lower surface 1606L.

Although upper traces 1608 are illustrated as being embedded within upper surface 1606U of substrate core 1606, in other embodiments, upper traces 1608 are partially embedded into substrate core 1606 or completely on top of upper surface 1606U. Similarly, although lower traces 1612 are illustrated as being embedded within lower surface 1606L of substrate core 1606, in other embodiments, lower traces 1612 are partially embedded into substrate core 1606 or completely on top of lower surface 1606L.

Substrate 1602 further includes dielectric solder masks 1607, 1609 on upper surface 1606U and lower surface 1606L, respectively. For example, upper solder mask 1607 protects, i.e., covers, first portions of upper traces 1608 while exposing second portions, e.g., lands 1610, of upper traces 1608. Lower solder mask 1609 protects, i.e., covers, first portions of lower traces 1612 while exposing second portions, e.g., terminals 1614 and lands 1615, of lower traces 1612. One or both of upper and lower solder masks 1607, 1609 are optional, and in one embodiment, are not formed.

Generally, substrate 1602 includes an upper, e.g., first, surface 1602U and an opposite lower, e.g., second, surface 1602L. Upper surface 1602U is defined by upper solder mask 1607, by upper surface 1606U of substrate core 1606, and/or by any other structure which forms upper surface 1602U of substrate 1602. Similarly, lower surface 1602L is defined by lower solder mask 1609, by lower surface 1606L of substrate core 1606, and/or by any other structure which forms lower surface 1602L of substrate 1602.

Although a particular electrically conductive pathway between upper traces 1608 and lower traces 1612 is described above, other electrically conductive pathways can be formed. For example, contact metallizations can be formed between the various electrical conductors.

Further, instead of straight through vias 1616, in one embodiment, a multilayer substrate includes a plurality of vias and/or internal traces that form the electrical interconnection between upper traces 1608 and lower traces 1612. In yet another embodiment, upper traces 1608 and vias 1616 are not formed.

In one embodiment, lands 1615 are distributed in an array. Conductive columns 1617, e.g., copper pillars having solder tips, solder balls, or other electrically conductive structure, are formed on lands 1615. For example, conductive columns 1617 are used for board/test socket connection. Although conductive columns 1617 are illustrated in FIG. 16, in another embodiment, conductive columns 1617 are formed at a later stage of fabrication, e.g., after attachment of a lid as discussed below.

In another embodiment, conductive columns 1617 are not formed. For example, exposed lands 1615 form a Land Grid Array (LGA).

Substrate 1602 includes a lid cavity 1618. Lid cavity 1618 is an opening extending through substrate 1602 and exposing standoff pattern 202 and active area 212. More particularly, lid cavity 1618 extends between upper surface 1602U and lower surface 1602L of substrate 1602.

Lid cavity 1618 is defined by lid cavity sidewalls 1620 of substrate 1602. Lid cavity sidewalls 1620 extend between upper surface 1602U and lower surface 1602L of substrate 1602.

Bond pads 214 are flip chip mounted to terminals 1614 of lower traces 1612 by flip chip bumps 1634, e.g., solder, copper, electrically conductive epoxy, or other electrically conductive material. Generally, flip chip bumps 1634 electrically and mechanically mount microfluidics sensor die 204 to substrate 1602. Microfluidics sensor die 204 is mounted to substrate 1602 such that active area 212 is aligned with lid cavity 1618.

A sealant 1636 is dispensed between microfluidics sensor die 204 and substrate 1602. More particularly, a dielectric sealant 1636, e.g., an underfill, is dispensed between active surface 206 of microfluidics sensor die 204 and lower surface 1602L of substrate 1602, e.g., adjacent sides 210 and/or through lid cavity 1618 adjacent lid cavity sidewalls 1620. Sealant 1636 seals the region between active surface 206 of microfluidics sensor die 204 and lower surface 1602L of substrate 1602. Sealant 1636 further encloses and protects flip chip bumps 1634 and generally enhances the bond between microfluidics sensor die 204 and substrate 1602.

In accordance with this embodiment, sealant 1636 extends between sides 210 of microfluidics sensor die 204 and lid cavity sidewalls 1620. Sealant 1636 forms a fluid tight seal between microfluidics sensor die 204 and substrate 1602 at lid cavity sidewalls 1620.

Microfluidics sensor package 1600 further includes an optional heat sink 1638. Heat sink 1638 is formed of a thermally conductive material such as copper. Heat sink 1638 is mounted to inactive surface 208 of microfluidics sensor die 204, e.g., with a thermal interface material 1640, e.g., a thermal grease or epoxy.

Further, heat sink 1638 extends outward beyond sides 210 of microfluidics sensor die 204 and is mounted to lower surface 1602L of substrate 1602, e.g., with a heat sink adhesive 1642. Heat sink 1638 dissipates heat from microfluidics sensor die 204 as well as provides strength and integrity to microfluidics sensor package 1600, e.g., enhances the bond between microfluidics sensor die 204 and substrate 1602.

Figure 17:
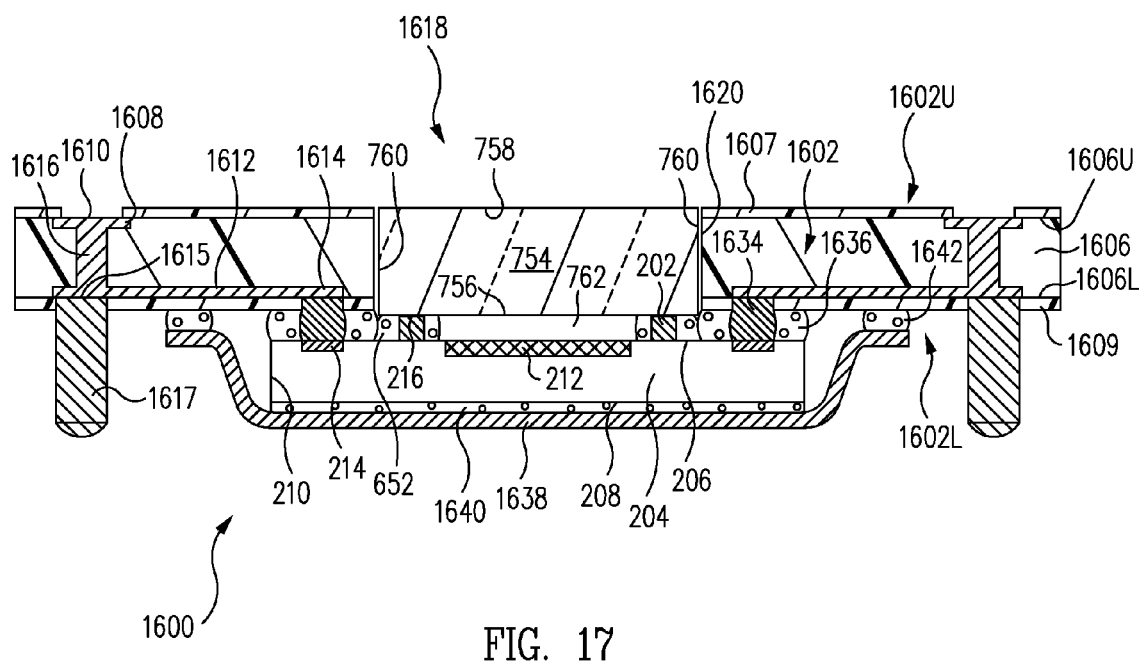
FIG. 17 is a cross-sectional view of the microfluidics sensor package of FIG. 16 at a later stage during fabrication in accordance with one embodiment.
Figure 18:
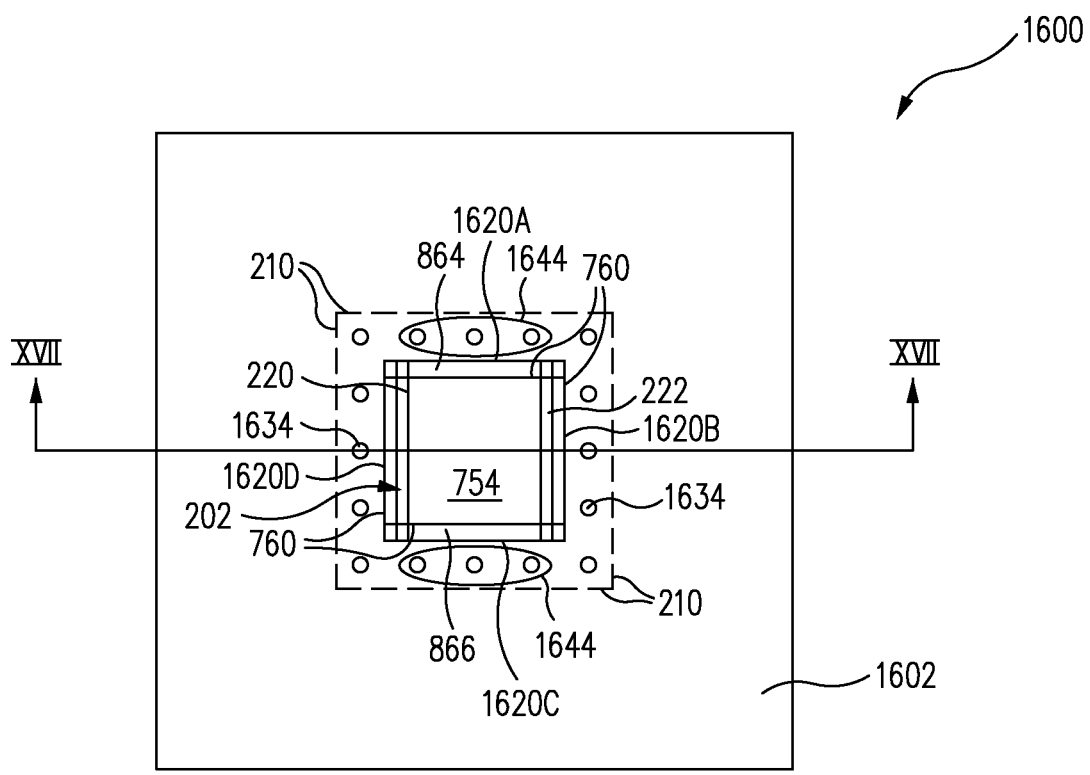
FIG. 18 is a top plan view of the microfluidics sensor package of FIG. 17 in accordance with one embodiment.

FIG. 17 is a cross-sectional view of microfluidics sensor package 1600 of FIG. 16 at a later stage during fabrication in accordance with one embodiment. FIG. 18 is a top plan view of microfluidics sensor package 1600 of FIG. 17 in accordance with one embodiment. Note the view of FIG. 17 corresponds to a cross-section view of FIG. 18 along the line XVII-XVII in accordance with one embodiment. Various features such as lands 1610 are not illustrated in FIG. 18 for simplicity.

Referring now to FIGS. 17 and 18 together, lid 754 is mounted to standoff pattern 202 by lid adhesive 652. Lid 754 is sometimes called a flat lid.

Lid cavity sidewalls 1620 include lid cavity sidewalls 1620A, 1620B, 1620C, 1620D. Lid cavity sidewalls 1620A, 1620B, 1620C, 1620D are collectively referred to as lid cavity sidewalls 1620.

Lid cavity sidewalls 1620A, 1620C are parallel to one another and perpendicular to lid cavity sidewalls 1620B, 1620D, which are parallel to one another. Lid cavity sidewalls 1620A, 1620C are sometimes called fluid port lid cavity sidewalls 1620A, 1620C as fluid generally flows in a direction parallel to lid cavity sidewalls 1620B, 1620D and between lid cavity sidewalls 1620A, 1620C.

Fluid port lid cavity sidewalls 1620A, 1620C of substrate 1602 and respective sides 760 of lid 754 define fluid ports 864, 866. More particularly, fluid ports 864, 866 are spaces, sometimes called channels, between fluid port lid cavity sidewalls 1620A, 1620C and respective sides 760, respectively. Fluid ports 864, 866 extend between the ambient environment and microfluidics cavity 762 and are generally defined between lid 754 and substrate 1602. Fluid ports 864, 866 are sometimes called entrance and exit ports.

During use of microfluidics sensor package 1600, fluid flows between fluid ports 864 and 866 or vice versa through microfluidics cavity 762 in a manner similar to that discussed above regarding FIG. 9.

Paying particular attention now to FIG. 18, sides 210 (the outline) of microfluidics sensor die 204, flip chip bumps 1634, and optionally dummy bumps 1644 are illustrated although it is to be understood that the features would be blocked by substrate 1620 and not be visible in the view of FIG. 18. In accordance with this embodiment, dummy bumps 1644 are formed between dummy bond pads of microfluidics sensor die 204 and dummy terminals of substrate 1602 in a manner similar to formation of flip chip bumps 1634 between bond pads 214 of microfluidics sensor die 204 and lands 1610 of substrate 1602. The dummy bond pads of microfluidics sensor die 204 and dummy terminals of substrate 1602 are similar to bond pads 214 of microfluidics sensor die 204 and lands 1610 of substrate 1602 however do not serve and electrical function, e.g., electrical signals are not carried by the dummy bond pads and the dummy terminals.

However, the dummy bumps 1644 are used to provide secure attachment of microfluidics sensor die 204 to substrate 1602. Formation of dummy bumps 1644 is optional. In one embodiment, dummy bumps 1644 and the associated dummy bond pads of microfluidics sensor die 204 and dummy terminals of substrate 1602 are not formed.

Figure 19:
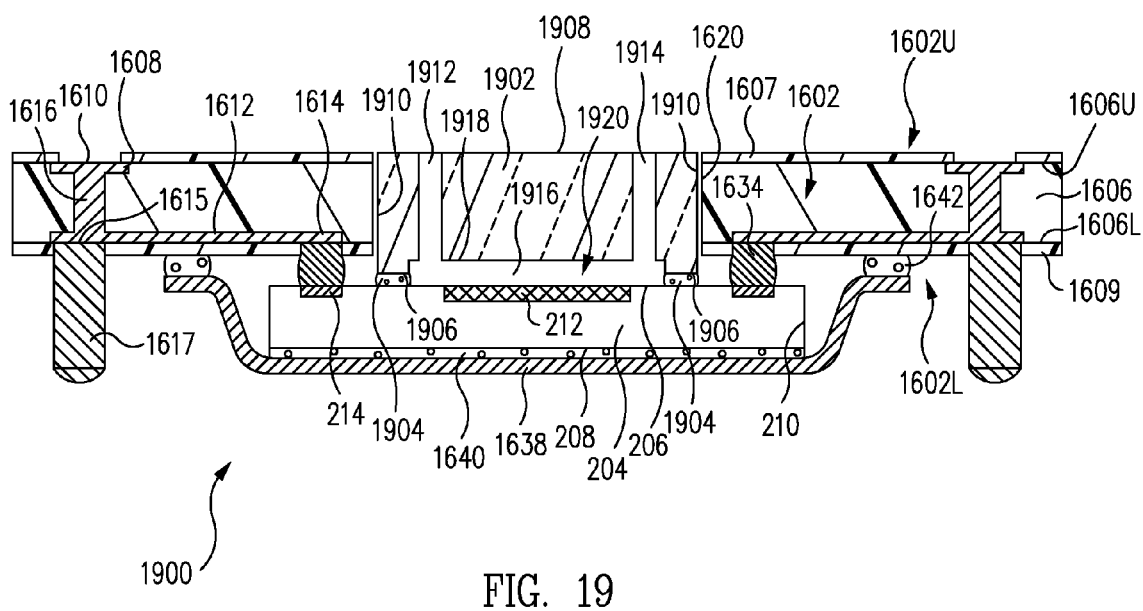
FIG. 19 is a cross-sectional view of a microfluidics sensor package in accordance with another embodiment.

FIG. 19 is a cross-sectional view of a microfluidics sensor package 1900 in accordance with another embodiment. Microfluidics sensor package 1900 of FIG. 19 is similar to microfluidics sensor package 1600 of FIG. 17 and only the significant differences are discussed below.

Referring now to FIG. 19, in accordance with this embodiment, microfluidics sensor package 1900 includes a structured lid 1902 mounted to active surface 206 with a structured lid adhesive 1904.

Structured lid 1902 includes an inner, e.g., first, surface 1906, an opposite outer, e.g., second, surface 1908, and sides 1910 extending perpendicularly between inner surface 1906 and outer surface 1908. Inner surface 1906 is mounted to active surface 206 with structured lid adhesive 1904.

Structured lid 1902 further includes ports 1912, 1914, and a channel 1916. Channel 1916 is defined by a recessed surface 1918 of structured lid 1902. Recessed surface 1918 and active surface 206 define a microfluidics cavity 1920. Inner surface 1906 is mounted to active surface 206 entirely around microfluidics cavity 1920 such that microfluidics cavity 1920 is a sealed cavity having ports 1912, 1914 extending thereto.

More particularly, ports 1912, 1914 extend between outer surface 1908 and recessed surface 1918. During use of microfluidics sensor package 1900, fluid flows between fluid ports 1912 and 1914 or vice versa through microfluidics cavity 1920 in a manner similar to that discussed above regarding FIG. 9.

Further, microfluidics sensor package 1900 is formed without sealant 1636 (see FIG. 17) as there is no need to form a fluid tight seal between microfluidics sensor die 204 and substrate 1602. However, in another embodiment, microfluidics sensor package 1900 is formed with sealant 1636, which accordingly is optional.

Figure 20:
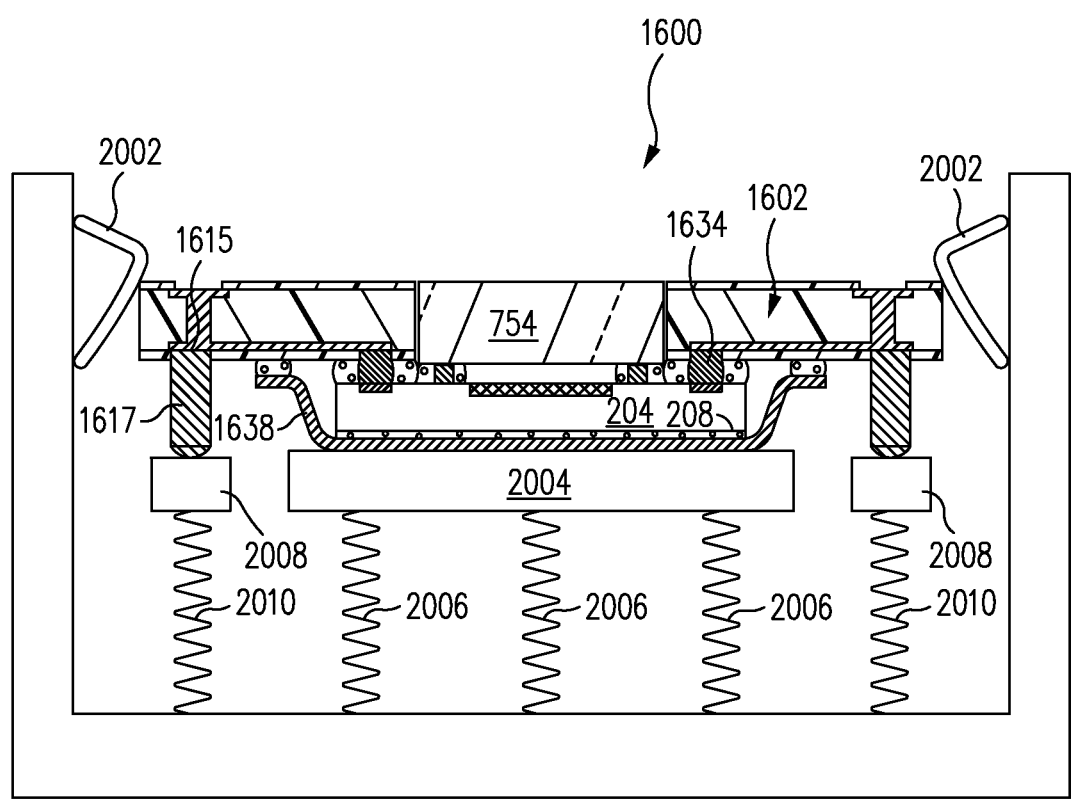
FIG. 20 is a cross-sectional view of the microfluidics sensor package of FIG. 17 within a test socket in accordance with one embodiment.

FIG. 20 is a cross-sectional view of microfluidics sensor package 1600 of FIG. 17 within a test socket 2000 in accordance with one embodiment. Microfluidics sensor package 1600 is pressed downwards past retaining springs 2002 of test socket 2000. A heat sink 2004 is pressed upwards against microfluidics sensor die 204 and optional heat sink 1638 by heat sink springs 2006. Contacts 2008 are pressed against and electrically connected to lands 1615 including optional conductive columns 1617 by contact springs 2010. Springs 2006, 2010 press microfluidics sensor package 1600 upward against retaining springs 2002 to mount microfluidics sensor package 1600 within test socket 2000.

Fluid is dispensed in a manner similar to that described above in regards to FIG. 9 and analysis is performed on the fluid. Input/output signals associated with the analysis are provide from/to contacts 2008. Heat is dissipated by heat sink 2004.

FIG. 20 provides one example of a test socket configuration for microfluidics sensor package 1600. However, microfluidics sensor package 1600 can be used in a variety of testing apparatuses or configurations depending upon the particular application.

Although specific embodiments were described herein, the scope of the invention is not limited to those specific embodiments. Numerous variations, whether explicitly given in the specification or not, such as differences in structure, dimension, and use of material, are possible. The scope of the invention is at least as broad as given by the following claims.

What is claimed is:

1. A structure comprising:
   a sensor die comprising:
   an active surface;
   a bond pad at the active surface; and
   an active area at the active surface;
   a standoff pattern coupled to the active surface;
   a lid; and
   a lid adhesive coupling the lid to the standoff pattern, wherein the sensor die comprises:
   an electrically conductive through via coupled to the bond pad, the through via extending between the active surface and an inactive surface of the sensor die, the through via comprising an inactive surface terminal at the inactive surface, the structure further comprising:
   a substrate; and
   a flip chip bump coupling the inactive surface terminal to a terminal of the substrate.

2. The structure of claim 1, further comprising a substrate, wherein the sensor die is a microfluidics sensor die, and an inactive surface of the microfluidics sensor die is coupled to the substrate.

3. The structure of claim 2 wherein the inactive surface of the microfluidics sensor die is coupled to a die pad of the substrate, the structure further comprising a bond wire coupling the bond pad to a lead of the substrate.

4. The structure of claim 1, further comprising: a first fluid port, a second fluid port, and a fluid channel between the first and second fluid ports.

5. The structure of claim 1 wherein the standoff pattern comprises two bars.

6. The structure of claim 5 wherein the sensor die comprises a plurality of bond pads, wherein the bond pad is one of the plurality of bond pads, and the bars are located on the active surface between at least some of the plurality of bond pads and the active area.

7. The structure of claim 5 wherein the standoff pattern further comprises dummy bumps.

8. The structure of claim 5 wherein the standoff pattern further comprises sub-channel bars between the bars.

9. The structure of claim 8 wherein the standoff pattern further comprises diverter bars.

10. The structure of claim 9 wherein the diverter bars define a variable cavity having a varying width and the sub-channel bars define a fixed cavity having a fixed width.

11. The structure of claim 1 wherein the standoff pattern comprises bar bump columns comprising bar bumps in a line.

12. A structure comprising:
    a sensor die comprising:
    an active surface; and
    an active area at the active surface;
    a standoff pattern coupled to the active surface;
    a package body comprising lid cavity sidewalls defining a lid cavity exposing the standoff pattern and the active area; and
    a lid, wherein fluid ports are defined by sides of the lid and the lid cavity sidewalls,
    wherein:
    the standoff pattern comprises a lid surface at a height from the active surface, and
    the lid comprises a planar first surface located at the height.

13. The structure of claim 12 further comprising a lid adhesive coupling the lid to the standoff pattern, wherein the lid, the lid adhesive, and the active surface define a cavity, the fluid ports extending between the cavity and an ambient environment.

14. The structure of claim 12 wherein the sensor die further comprises a bond pad at the active surface, the structure further comprising:
    a substrate comprising a terminal; and
    a bond wire coupling the bond pad to the terminal, wherein the package body encloses the bond pad, the bond wire, and the substrate.

15. A structure comprising:
    a sensor die comprising:
    an active surface;
    a bond pad at the active surface; and
    an active area at the active surface;

a standoff pattern coupled to the active surface;
a lid; and
a lid adhesive coupling the lid to the standoff pattern,
a substrate comprising a terminal; and
a flip chip bump coupling the bond pad to the terminal.

16. The structure of claim 15 wherein the substrate comprises lid cavity sidewalls defining a lid cavity exposing the standoff pattern and the active area, wherein fluid ports are defined by sides of the lid and the lid cavity sidewalls.

17. The structure of claim 15 wherein the substrate further comprises traces comprising the terminal and a land, the structure further comprising a conductive column coupled to the land.

18. The structure of claim 15 further comprising:
a heat sink coupled to an inactive surface of the sensor die and to the substrate.

\* \* \* \* \*